(12) United States Patent
Chen et al.

(10) Patent No.: US 12,274,673 B1
(45) Date of Patent: Apr. 15, 2025

(54) CLOSED TYPE MEDICINE LIQUID TRANSFER DEVICE AND SYSTEM WITH DOUBLE-CHAMBER INTERNAL CIRCULATION

(71) Applicant: GUANGDONG JIANLIYUAN MEDICAL TECHNOLOGY CO., LTD., Guangdong (CN)

(72) Inventors: Rizhi Chen, Guangdong (CN);
Rongqiong Luo, Guangdong (CN);
Shigeng Xie, Guangdong (CN);
Weiquan Chen, Guangdong (CN);
Binghua Tang, Guangdong (CN);
Liangyu Zheng, Guangdong (CN);
Lizhen Yang, Guangdong (CN)

(73) Assignee: GUANGDONG JIANLIYUAN MEDICAL TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 18/839,828

(22) PCT Filed: Mar. 2, 2023

(86) PCT No.: PCT/CN2023/079355
§ 371 (c)(1),
(2) Date: Aug. 20, 2024

(87) PCT Pub. No.: WO2024/066201
PCT Pub. Date: Apr. 4, 2024

(30) Foreign Application Priority Data

Sep. 30, 2022 (CN) .......................... 202211212995.9

(51) Int. Cl.
*A61J 1/20* (2006.01)
*A61M 5/24* (2006.01)
*A61M 5/32* (2006.01)

(52) U.S. Cl.
CPC .......... *A61J 1/2096* (2013.01); *A61M 5/2448* (2013.01); *A61M 5/32* (2013.01)

(58) Field of Classification Search
CPC ....... A61J 1/2096; A61M 5/2448; A61M 5/32
See application file for complete search history.

(56) References Cited

U.S. PATENT DOCUMENTS 4,874,368 A * 10/1989 Miller .............. A61B 17/00491
604/82
6,224,568 B1 5/2001 Morimoto et al.
(Continued)

FOREIGN PATENT DOCUMENTS

| CN | 1775317 A | 5/2006 |
| CN | 101466344 A | 6/2009 |

(Continued)

OTHER PUBLICATIONS

International Search Report for PCT/CN2023/079355 mailed on Jun. 25, 2023.

(Continued)

*Primary Examiner* — Dung T Ulsh
(74) *Attorney, Agent, or Firm* — The PL Law Group, PLLC

(57) ABSTRACT

A medicine liquid transfer device includes a double-chamber syringe, a dispensing needle assembly, and a syringe needle sealing assembly. The medicine liquid transfer device features an exquisite structural design and easy assembly, enables fully-closed medicine preparation and transfer, and allows automatic or manual adjustment and balance of the air pressure inside the medicine container in use, thereby minimizing the risk of medicine leakage and providing an excellent leakproof effect, while having advantages of low cost, high convenience of use, and the like.

20 Claims, 6 Drawing Sheets

(56) References Cited

U.S. PATENT DOCUMENTS

| | | | |
|---|---|---|---|
| 2003/0233067 A1* | 12/2003 | McIntosh | A61B 17/00491 604/82 |
| 2005/0182357 A1 | 8/2005 | Snell et al. | |
| 2012/0035532 A1 | 2/2012 | Melsheimer et al. | |
| 2015/0224258 A1* | 8/2015 | Holtwick | A61M 5/20 604/207 |
| 2017/0333286 A1 | 11/2017 | Phipps | |
| 2019/0053982 A1 | 2/2019 | Momose et al. | |
| 2020/0238009 A1* | 7/2020 | Koh | A61L 24/104 |
| 2022/0265938 A1* | 8/2022 | Guo | A61M 11/06 |

FOREIGN PATENT DOCUMENTS

| | | |
|---|---|---|
| CN | 104800079 A | 7/2015 |
| CN | 111346008 A | 6/2020 |
| CN | 111346009 A | 6/2020 |
| CN | 111417413 A | 7/2020 |
| CN | 111714369 A | 9/2020 |
| CN | 112999465 A | 6/2021 |
| CN | 215584844 U | 1/2022 |
| CN | 215741026 U | 2/2022 |
| CN | 114288181 A | 4/2022 |
| CN | 216725427 U | 6/2022 |
| CN | 216908634 U | 7/2022 |
| CN | 115607444 A | 1/2023 |
| EP | 0 417 988 A1 | 3/1991 |
| JP | 2000-042106 A | 2/2000 |
| JP | 2010-512948 A | 4/2010 |
| JP | 2010-524626 A | 7/2010 |
| WO | WO 2021/184568 A1 | 9/2021 |
| WO | WO 2021/188904 A1 | 9/2021 |

OTHER PUBLICATIONS

Office action issued on Jan. 14, 2025 from Japan Intellectual Property Office in a counterpart Japanese Patent Application No. 2024-547926 (all the cited references are listed in this IDS.) (English translation is also submitted herewith.).

European Search Report For EP 23869464.0 issued on Feb. 24, 2025 from European patent office in a counterpart European patent application (See the highlight sentences of Part 1, pp. 1-3, the highlight sentences of. Part 2, p. 3, the highlight sentences of Part 3, p. 4, the highlight sentences of Part 9, p. 5).

* cited by examiner

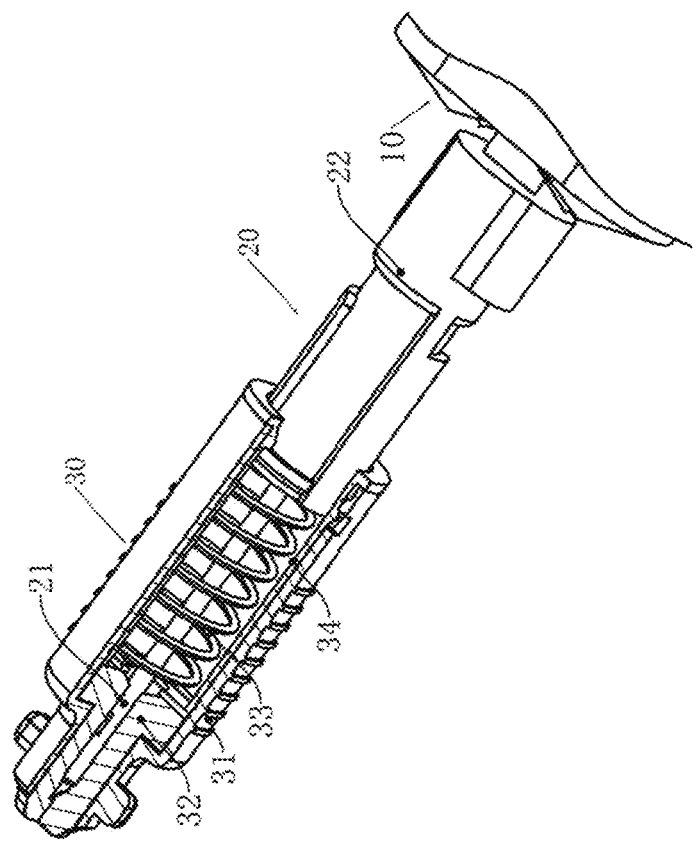
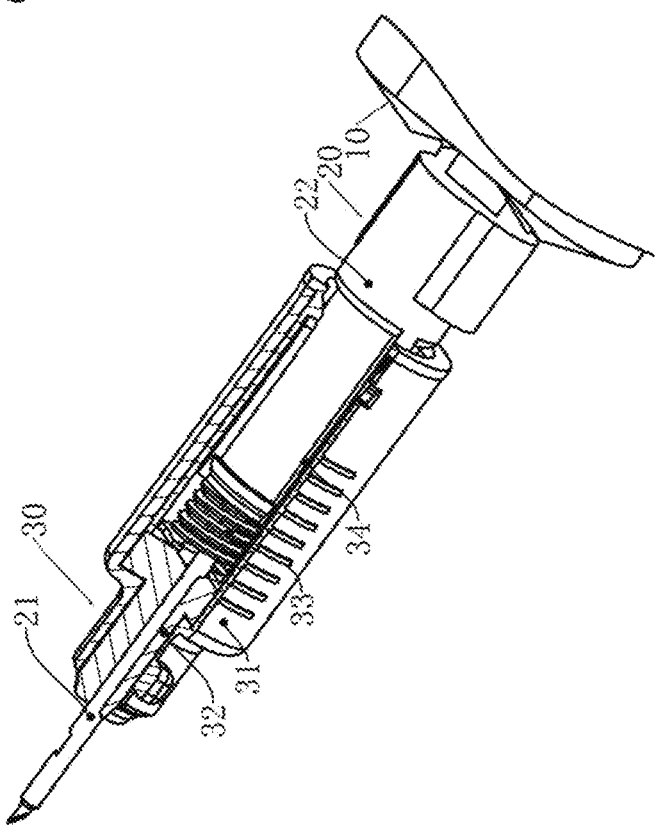
FIG. 2A
FIG. 2B

CLOSED TYPE MEDICINE LIQUID TRANSFER DEVICE AND SYSTEM WITH DOUBLE-CHAMBER INTERNAL CIRCULATION

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/CN2023/079355, filed Mar. 2, 2023, which claims priority to the benefit of Chinese Patent Application No. 202211212995.9 filed in the China Intellectual Property Office on Sep. 30, 2022, the entire contents of which are incorporated herein by reference.

BACKGROUND

1. Technical Field

The present disclosure belongs to the field of medicine preparation and transfer devices, and specifically relates to closed type medicine liquid transfer device and system with double-chamber internal circulation.

2. Background Art

Dangerous medicines represented by chemotherapy medicines have great harm to health of medical workers who are engaged in preparation and transportation of the medicines for a long time, such as causing cancers, internal organ injury, DNA damage, reproductive problems, abortion and teratogenesis and the like. The existing data show that pharmacists, nurses and other personnel who are in long-term contact with dangerous medicines have a risk of cancer incidences being increased by 3 to 10 times and a risk of infertility or abortion and the like increased by 2 to 5 times compared with common people. In view of this, facilities such as various purification rooms and biological cabinets are built in some medical institutions to reduce the risk of medicine leakage, which involve high investment cost but bring about poor popularization and application effects in practice. There is a great demand, but few choices, for closed type medicine liquid transfer devices in domestic diagnosis and treatment links, because the product is required to have good leak-proofness, but low cost and convenient use. The American BD company has recently introduced a closed type configuration and transportation system, but the system is difficult to popularize due to the complex structure, high cost and complicated operation, and can only reduce the leakage risk by 50% to 80%. The applicant of the present disclosure has also proposed two types of medicine liquid transfer devices (CN111346008A and CN111346009A) equipped with air bags for balancing the air pressure, which have low cost, convenient use and better internal circulation closing effect, but also have some problems in popularization and application, such as easy breakage/detachment of the air bag structure, blockage due to easy infiltration of medicine liquid into the channel connecting the air bags, or the like, and therefore still involve a certain risk of leakage.

SUMMARY

Aiming at the defects of the existing art and the practical application requirements, a main object of the present disclosure is to provide closed type medicine liquid transfer device and system with double-chamber internal circulation, which feature an exquisite structural design and easy assembly, enables fully-closed medicine preparation and transfer, and allows automatic or manual adjustment and balance of the air pressure inside the medicine container in use, thereby minimizing the risk of medicine leakage and providing an excellent leakproof effect, while having advantages of low cost, high convenience of use, and the like.

To achieve the above object, as a first aspect of the present disclosure, there is provided a closed type medicine liquid transfer device with double-chamber internal circulation, including a double-chamber syringe, a dispensing needle assembly, and a syringe needle sealing assembly, characterized in that:

the double-chamber syringe consists of a first syringe barrel, a first piston rod slidable back and forth along an inner cavity in the first syringe barrel, a second syringe barrel, and a second piston rod slidable back and forth along the inner cavity in the second syringe barrel, where the first syringe barrel and the second syringe barrel are fixedly arranged in parallel, in the same direction and with flush front ends: a first joint is provided on a front end face of the first syringe barrel, and a second joint is provided on a front end face of the second syringe barrel;

the dispensing needle assembly includes a dispensing needle and a needle seat, where the dispensing needle is fixedly connected to the needle seat with a rear end of the dispensing needle embedded into a front end of the needle seat; where a rear end of the needle seat is provided with a first connection hole matched with the first joint and a second connection hole matched with the second joint, and the needle seat is internally provided with a first channel and a second channel in communication with the first connection hole and the second connection hole respectively and independent of each other;

the dispensing needle is a double-layer columnar structure including an inner columnar channel and a side annular channel; where the inner columnar channel is in communication with the first channel, and the side annular channel is in communication with the second channel;

the dispensing needle assembly is fixed and closely connected to the double-chamber syringe by embedding the first joint and the second joint into the first connection hole and the second connection hole, respectively;

the syringe needle sealing assembly includes a sheath, a closing member and an elastic member arranged coaxially with the dispensing needle; where the sheath is a hollow cylindrical structure with front and back openings, and is movable axially and sleeved onto the front end of the needle seat;

the closing member is made of an elastic material, fixedly disposed inside a front barrel of the sheath: a pore channel for passage of the dispensing needle is provided at a central axis of the closing member, and has an inner diameter smaller than an outer diameter of the dispensing needle;

the elastic member is provided between the closing member and the needle seat, and provides axial elastic support for the closing member at the front end against the needle seat;

in a non-pressed state, the elastic member extends axially so that the sheath shields the dispensing needle inside, and under an elastic force of the elastic material, the closing member tightly wraps a front end part of the dispensing needle and seals front channel openings of the inner columnar channel and the side annular channel inside; and in a pressed state, the elastic member is axially compressed, and the front end part of the dispensing needle, including the front channel openings of the inner columnar channel and the side annular channel, penetrates out of the sheath through the pore channel in the closing member.

In the present disclosure, unless otherwise specified, the front end refers to an end to which a needle tip of the dispensing needle is pointed, and the rear end refers to an opposite end to the front end.

In the closed type medicine liquid transfer device of the present disclosure, the double-chamber syringe consists of a first syringe barrel, a first piston rod slidable back and forth along an inner cavity in the first syringe barrel, a second syringe barrel, and a second piston rod slidable back and forth along the inner cavity in the second syringe barrel, and the first syringe barrel and the second syringe barrel are fixedly arranged in parallel, in the same direction and with flush front ends. The dimensions of the first and second syringe barrels are not limited in the present disclosure, and may be the same or different. However, for ease of manufacture and practical operation, as a preferable implementation, the first and second syringe barrels have the same dimensions. Preferably, the first and second syringe barrels are each made of a transparent material, and provided with scales on a barrel surface to show the volume.

The joint on the front end face of each syringe barrel mainly has two functions: first, serving as a plug-in type fixed connecting member between the double-chamber syringe and the dispensing needle assembly, and second, serving as an inlet/outlet for a medicine liquid or gas to enter/exit the syringe barrel. Considering limitations on the dimension of the needle seat, the first and second joints are preferably arranged as close as possible.

As a preferable implementation, the first joint and the second joint each have an outer sidewall being a conical surface on which at least one annular boss is provided. Accordingly, the first connection hole and the second connection hole at the rear end of the needle seat each have a shape matched with the conical surface of the corresponding joint, and have a wall provided with an annular slot corresponding to the annular boss. With the joints and the connection holes fixed in a plug-in manner, the dispensing needle assembly can be fixed and closely connected to the double-chamber syringe conveniently.

In the closed type medicine liquid transfer device of the present disclosure, the dispensing needle assembly includes a dispensing needle and a needle seat, where the dispensing needle is fixedly connected to the needle seat with a rear end of the dispensing needle embedded into a front end of the needle seat.

The dispensing needle is a double-layer columnar structure including an inner columnar channel and a side annular channel. As a preferable implementation, the dispensing needle may consist of an inner needle tube and an outer needle tube, the inner needle tube is inserted in the outer needle tube, with both ends extending out of the outer needle tube, so that the inner columnar channel is formed by an inner cavity of the inner needle tube, and the side annular channel is formed by a cavity between the outer needle tube and the inner needle tube.

The inner needle tube and the outer needle tube may be independent of each other, or may be integrally formed and fixedly connected with each other. When the latter is selected, a front end of the outer needle tube is preferably fixedly connected to a front sidewall of the inner needle tube in a closed manner. Further preferably, the front end of the inner needle tube is provided as an inclined opening, or the front end of the inner needle tube is a pointed end provided with a side opening; and the front sidewall of the outer needle tube is provided with a side opening. Such an opening design is not only favorable to penetrating the dispensing needle into a medicine container, but also allows reduced interference between the inner columnar channel and the side annular channel. Meanwhile, if the side annular channel is taken as the medicine liquid channel, the side opening provided at a more rear position can better follow the operation habit of inverting the liquid medicine bottle of the medical personnel when preparing the medicine, which is favorable to absorbing the medicine liquid more completely (especially the medicine liquid at the bottleneck), thereby avoiding waste of the medicine or an increased operation risk caused by a second operation.

The needle seat is a carrier for providing the dispensing needle and the syringe needle sealing assembly. As described above, a rear end of the needle seat is provided with a first connection hole matched with the first joint and a second connection hole matched with the second joint, and the needle seat is internally provided with a first channel and a second channel in communication with the first connection hole and the second connection hole respectively and independent of each other; and the inner columnar channel of the dispensing needle is in communication with the first channel, and the side annular channel is in communication with the second channel.

As a preferable implementation, a front end part of the needle seat is provided with a mounting slot, in which a needle penetrating table with a configuration matched with the mounting slot is disposed (equivalent to digging out a portion of the front end part of the needle seat); the front end openings of the first channel and the second channel are both located at a bottom of the mounting slot, and the front end opening of the first channel is coaxial with the dispensing needle: a through pore channel is provided in the needle penetrating table at a position corresponding to an axis of the dispensing needle, and consists of a front needle penetrating hole and a rear fixing hole, where the needle penetrating hole is flared, with an inner diameter gradually reduced from front to back to the fixing hole, and an inner diameter of the fixing hole is matched with an outer diameter of the outer needle tube; and the needle penetrating table has a rear end face provided with a communication slot having two ends in communication with the second channel and the fixing hole, respectively. A rear end of the inner needle tube of the dispensing needle penetrates through the needle penetrating table to be fixed in the first channel in an embedding manner; and a rear end of the outer needle tube is fixed in the fixing hole of the needle penetrating table in an embedding manner.

Further preferably, in the above implementation, the first channel in the needle seat is disposed coaxially with the dispensing needle, and the second channel is disposed on one side of the first channel in parallel.

Further preferably, the needle penetrating table has a non-circular cross section that remains unchanged in an axial direction. With such a design, the needle penetrating table can be only installed into the mounting slot of the needle seat at a fixed angle, thereby facilitating accurate butting of the communication slot with the second channel at the bottom of the needle penetrating table.

With sufficient knowledge of the configurations of the needle seat and the dispensing needle, one skilled in the art can easily determine how to assemble the dispensing needle assembly. For example, when the dispensing needle consists of an inner needle tube and an outer needle tube independent of each other, the needle penetrating table may be taken out first, the rear end of the inner needle tube is embedded into the first channel, then the outer needle tube is fixed on the needle penetrating table, and then the integrated outer needle tube and needle penetrating table are sleeved outside the inner needle tube and inserted into the mounting slot: or when the inner needle tube and the outer needle tube are integrally formed and fixedly connected with each other, the needle penetrating table may be taken out first, and the dispensing needle is fixed on the needle penetrating table, ensuring that the rear end of the outer needle tube is embedded into the fixing hole in the needle penetrating table and the rear end of the inner needle tube penetrates out of the needle penetrating table, and then the needle penetrating table is inserted into the mounting slot, ensuring that the rear end of the exposed inner needle tube is completely embedded into the first channel.

When the dispensing needle assembly is fixed and closely connected to the double-chamber syringe, the inner columnar channel, the first channel, the first connection hole and the first syringe barrel are sequentially communicated from front to back to form a closed passage I; and the side annular channel, the second channel, the second connection hole and the second syringe barrel are sequentially communicated from front to back to form a closed passage II. The closed passages I and II are independent of each other. In the medicine liquid preparation and transfer process, one of the passages is used for conveying the medicine liquid, while the other functions to convey a gas and balance the air pressure.

In the present disclosure, the syringe needle sealing assembly includes a sheath, a closing member and an elastic member arranged coaxially with the dispensing needle. The syringe needle sealing assembly can not only prevent prickling, but also ensure a totally closed state throughout the whole medicine liquid preparation and transfer process, thereby avoiding a risk of medicine liquid leakage from the front channel openings. Assemblies with similar structures and functions have been reported in previous patents of the inventive applicant, for example, CN111346008A and CN111346009A, but the manufacturing process is relatively complex and requires the use of relatively complex structural members, rather than assembly of simple structural members, and therefore, the mass production requires the use of specific equipment or has high requirements on the precision of the equipment.

To achieve the purposes of simplifying the manufacturing process, facilitating assembly and further reducing the mass production cost, the applicant optimizes the structure of the syringe needle sealing assembly. As a preferable implementation of the present disclosure, the syringe needle sealing assembly includes a sheath, a closing member, an elastic member and an inner sleeve coaxially arranged, where:

a front end part of the sheath has a smaller radial dimension to form a composite cylindrical structure consisting of a first cylindrical section with a smaller inner diameter and a second cylindrical section with a larger inner diameter;

the closing member is designed as a structure having an inverted T-shaped cross section with a front diameter corresponding to the inner diameter of the first cylindrical section and a rear diameter corresponding to the inner diameter of the second cylindrical section, so that the closing member is capable of at least partially filling an inner cavity of the second cylindrical section while completely filling an inner cavity of the first cylindrical section;

an inner diameter of the inner sleeve corresponds to the outer diameter of the needle seat, an outer diameter of the inner sleeve corresponds to the inner diameter of the second cylindrical section of the sheath, and a front end face of the inner sleeve is closed and has a through hole for passage of the dispensing needle in a center of the end face; the inner sleeve is fixedly connected in the second cylindrical section of the sheath, with the front end face abutting against a rear end face of the closing member; and the elastic member is provided in the inner sleeve, with two ends abutting against a front end inner surface of the inner sleeve and a front end face of the needle seat.

By improving the structures of the sheath and the closing member and adding the inner sleeve, a position of the closing member is limited and fixed, and both ends of the elastic member abut against a hard material, so that the overall structure and performance are more stable. Further preferably, a snap is provided on an outer wall the inner sleeve, and a corresponding snap hole is provided in the second cylindrical section of the sheath, so that when the inner sleeve is inserted into the sheath, the sheath is fixedly connected to the inner sleeve by the snap matched with the snap hole. Preferably, an annular boss is provided at a rear end opening of the inner sleeve in a radially outward mode, and when the front end face of the inner sleeve abuts against the rear end face of the closing member, the annular boss at the rear end is exposed to the sheath and abuts against a rear end of the sheath.

It will be readily appreciated that in use of the medicine liquid transfer device of the present disclosure, the syringe needle sealing assembly, although moved axially with extension and retraction of the elastic member, remains connected to the needle seat. As a preferable implementation, snap structures are provided on both the front end inner surface of the inner sleeve and the front end face of the needle seat to enable fixed connection to the elastic member. As still another preferable implementation, an L-shaped slot consisting of an axial slot and a lateral slot (perpendicular to the axial slot) is formed on a side face of the needle seat, and a sliding table is provided at the rear end of the inner sleeve in a radially inward direction and embedded into and slidable along the L-shaped slot. Through the position design of the sliding table and the L-shaped slot, a movement range of the syringe needle sealing assembly relative to the needle seat can be flexibly adjusted and limited. As the sliding table slides backward along the axial slot, the elastic member is compressed, and the dispensing needle penetrates out of the closing member, and when a preset degree is reached, the sliding table is rotated along the lateral slot to limit the axial movement of the syringe needle sealing assembly, thereby achieving the effect of limiting and fixing.

The closing member is made of an elastic material, preferably any one of rubber, silicone, or synthetic rubber. A suitable elastic material should meet the relevant standards for medical materials, as will be readily known and determined by those skilled in the art. As a preferable implementation, a front end face of the closing member protrudes out of a front end face of the sheath, so that the closing member made of an elastic material can be closely attached to a rubber opening of the medicine container in preparation and transfer of the medicine liquid, thereby better sealing the opening of the medicine container.

The elastic member may be an elastic foldable tube, a spring or the like, and preferably a spring.

When the closed type medicine liquid transfer device of the present disclosure is used for medicine liquid preparation and transfer operation by matching with a liquid transfer connector, two snap tables protruding radially outward are preferably disposed symmetrically on a front end outer wall of the sheath to enable fixed connection to the liquid transfer connector.

In the closed type medicine liquid transfer device of the present disclosure, in a non-pressed state, the elastic member extends axially so that the sheath shields the dispensing needle inside, and under an elastic force of the elastic material, the closing member tightly wraps a front end part of the dispensing needle and seals front channel openings of the inner columnar channel and the side annular channel inside; and in a pressed state, the elastic member is axially compressed, and the front end part of the dispensing needle, including the front channel openings of the inner columnar channel and the side annular channel, penetrates out of the sheath through the pore channel in the closing member. The initial state of the closed type medicine liquid transfer device may be a non-pressed state or a pressed state, but the non-pressed state is preferably for purposes of preventing prickling, contamination, and inertial deformation of the elastic member and the closing member.

Preferably, the closed type medicine liquid transfer device of the present disclosure further includes a protective cap. In a standby state, the protective cap is sleeved on the sheath to avoid potential contamination risks.

As a second aspect of the present disclosure, there is further provided a closed type medicine liquid transfer system, including:
  the closed type medicine liquid transfer device with double-chamber internal circulation as described above, and a liquid transfer connector configured to fixedly connecting the medicine liquid transfer device to a medicine container; where
  one end of the liquid transfer connector is configured to fixedly connect the medicine container in a detachable manner, and the other end of the liquid transfer connector is configured to fixedly connect the medicine liquid transfer device in a detachable manner; and in fixed connection, a front end face of a closing member abuts against a container opening of the medicine container.

As a preferable implementation, the liquid transfer connector includes a first sleeve and a second sleeve coaxially arranged and connected with each other, where the first sleeve is configured to be detachably sleeved onto a front end of a sheath of the medicine liquid transfer device, and the second sleeve is configured to be detachably sleeved onto the container opening of the medicine container, and in fixed connection, the front end face of the closing member and the container opening of the medicine container are stably abutted in the sleeves.

Further preferably, snap claws extending forward axially are disposed symmetrically on outer edges of the second sleeve, release arms extending backward are provided on rear ends of the respective snap claws, and the second sleeve is fixed to the container opening by the snap claws and removable from the container opening by the release arms.

Further preferably, two snap slots, each having an L-shaped structure consisting of an axial slot and a lateral slot, are disposed symmetrically on an inner wall of the first sleeve, and correspondingly, two snap tables protruding radially outward are disposed symmetrically on a front end outer wall of the sheath. When the sheath is inserted into the first sleeve, the snap tables enters the axial slots of the snap slots synchronously, and when the sheath reaches a preset position, the medicine liquid transfer device is rotated to enable the snap tables to rotate into the lateral slots, so that the medicine liquid transfer device is fixed to the liquid transfer connector; and disassembly and separation can be implemented by a reverse operation.

The closed type medicine liquid transfer device of the present disclosure features double-chamber internal circulation, where the closed passages I and II are independent of each other, the closed passage I is in communication with a first syringe barrel and a medicine container, and the closed passage II is in communication with a second syringe barrel and the medicine container. When the front end part of the dispensing needle is penetrated into the medicine container, one of the first syringe barrel and the second syringe barrel is used for conveying the medicine liquid, while the other can balance the air pressure through back and forth movement of the piston rod in cooperation with air sucked in advance in the syringe barrel.

The closed type medicine liquid transfer device of the present disclosure may be used for purposes of preparing a mixed medicine, transporting a prepared medicine liquid into an infusion bottle or an indwelling needle and the like. It will be readily apparent to those skilled in the art how to use the above-described closed type medicine liquid transfer device and system of the present disclosure for medicine liquid preparation and transfer with a full understanding of the construction of the closed type medicine liquid transfer device and system.

Taking the case of preparing a medicine liquid (related to dissolving medicine powder) and injecting it back into an infusion bottle as an example, the process of using the medicine liquid transfer system of the present disclosure may include the following steps:
  (1) pulling a first piston rod of the double-chamber syringe backward, until a volume of a front cavity of the first syringe barrel is larger than a volume of the medicine liquid to be prepared, where to complete this step of storing air, the dispensing needle may be penetrated out of the closing member in advance, and then reset after the air storage, or the double-chamber syringe may be separated from the dispensing needle assembly, and then fixedly connected to the dispensing needle assembly again after the air storage;
  (2) sleeving a second sleeve of a liquid transfer connector A on a mouth of an infusion bottle and fixing the two by snap claws, and then holding a sheath (provided with snap tables) of the medicine liquid transfer device to align the sheath with a first sleeve (provided with snap slots) inserted into the liquid transfer connector A, and rotating the sheath to fix, in which case a front end face of the closing member abuts against a rubber opening of the infusion bottle in the sleeves;
  (3) holding and pushing forward a syringe barrel of the medicine liquid transfer device, so that the dispensing needle penetrates through the closing member into the infusion bottle with compression of the spring; and rotating the syringe barrel (for example, clockwise) when the dispensing needle is completely penetrated in, so that the syringe needle sealing assembly is limited and fixed to the needle seat;
  (4) pulling a second piston rod of the double-chamber syringe to extract part of the medicine liquid (such as physiological saline) in the infusion bottle into the second syringe barrel through the closed passage II, in which case a negative pressure is generated in the infusion bottle, so that the first piston rod is moved forward under an action of an internal and external pressure difference, and the air reserved in the first syringe barrel is supplemented into the infusion bottle until the internal and external air pressures are balanced;

(5) rotating the syringe barrel reversely (for example, anticlockwise) when the medicine liquid is extracted, to release the limiting and fixing of the syringe needle sealing assembly and the needle seat, and moving the double-chamber syringe and the dispensing needle assembly backward under an elastic potential energy of the spring until the dispensing needle is reset, that is, until the dispensing needle is withdrawn from the infusion bottle and sealed by the closing member again;

(6) screwing a sheath of the medicine liquid transfer device to release the fixed connection between the medicine liquid transfer device and the liquid transfer connector A, and pulling the medicine liquid transfer device from the liquid transfer connector A;

(7) sleeving a second sleeve of a liquid transfer connector B on a mouth of a penicillin bottle and fixing the two with snap claws, and then holding the sheath of the medicine liquid transfer device to align the sheath with a first sleeve (provided with snap slots) inserted into the liquid transfer connector B, and rotating the sheath to fix, in which case a front end face of the closing member abuts against a rubber opening of the penicillin bottle in the sleeves;

(8) holding and pushing forward a syringe barrel of the medicine liquid transfer device, so that the dispensing needle penetrates through the closing member into the penicillin bottle with compression of the spring, and rotating the syringe barrel (for example, clockwise) when the dispensing needle is completely penetrated in, so that the syringe needle sealing assembly is limited and fixed to the needle seat;

(9) pushing a second piston rod of the double-chamber syringe so that the medicine liquid is injected into the penicillin bottle from the second syringe barrel through a closed passage II, in which case a positive pressure is generated in the penicillin bottle, and air in the penicillin bottle automatically enters the first syringe barrel through the closed passage I to push the first piston rod to move backward;

(10) when the original medicinal powder in the penicillin bottle is fully dissolved by the medicine liquid injected into the penicillin bottle, pulling the second piston rod to extract the mixed medicine liquid from the penicillin bottle to the second syringe barrel through the closed passage II, in which case a negative pressure is generated in the penicillin bottle, the gas in the first syringe barrel is automatically supplemented into the penicillin bottle so that the first piston rod is moved forward under an internal and external pressure difference until the internal and external air pressures are balanced;

(11) when the mixed medicine liquid is extracted, referring to steps (5) and (6), resetting the dispensing needle and pulling the medicine liquid transfer device out of the liquid transfer connector B;

(12) holding the sheath of the medicine liquid transfer device to align the sheath with the first sleeve inserted into the liquid transfer connector A again, and rotating the sheath to fix, in which case the front end face of the closing member abuts against the rubber opening of the infusion bottle in the sleeves again;

(13) after the operation referring to the step (3) is performed, pushing the second piston rod of the double-chamber syringe to inject the mixed medicine liquid into the infusion bottle from the second syringe barrel through the closed passage II, in which case a positive pressure is generated in the infusion bottle, and air in the penicillin bottle automatically enters the first syringe barrel through the closed passage I to push the first piston rod to move backward; and

(14) when the mixed medicine liquid is completely injected into the infusion bottle, referring to steps (5) and (6), resetting the dispensing needle and pulling the medicine liquid transfer device out of the liquid transfer connector A.

In the preparation and transfer process discussed above, the second syringe barrel transports the medicine liquid through the closed passage II, while the first syringe barrel balances the internal and external air pressure of the transfer system by moving the first piston rod back and forth and in cooperation with the air sucked in advance in the first syringe barrel. The back and forth movement of the first piston rod may be implemented under an action of the internal and external pressure difference only without intervention of an external force, or may be assisted by manpower to flexibly adjust the process.

Compared with the existing art, the beneficial effects of the present disclosure include at least the following aspects:

(1) the medicine liquid transfer device of the present disclosure has an exquisite structural design, in which all components are convenient for batch production and assembly, and components with relatively complex structures and special equipment are not needed;

(2) the product has stable structure and performance, low cost, high yield and convenient use;

(3) the internal and external air pressures of the medicine liquid transfer system are completely balanced during the process of medicine preparation and transfer; and (4) fully-closed medicine preparation and transfer can be realized, thereby minimizing the risk of medicine leakage and providing an excellent leakproof effect.

The present disclosure will be further described below in conjunction with the drawings.

BRIEF DESCRIPTION OF THE DRAWINGS

FIG. 1A shows the medicine liquid transfer device in a non-pressed state, and FIG. 1B shows the medicine liquid transfer device in a pressed state;

FIGS. 2A and 2B are a partial perspective sectional view of the medicine liquid transfer device in embodiment 1, where FIG. 2A shows the medicine liquid transfer device in a non-pressed state, and FIG. 2B shows the medicine liquid transfer device in a pressed state;

FIG. 4A shows a disconnected state, FIG. 4B shows a connected state, and FIG. 4C shows the medicine liquid transfer system in an operating state;

DETAILED DESCRIPTION OF THE INVENTION

To better illustrate the objects, technical solutions and advantages of the present disclosure, the specific implementations of the present disclosure is further described in detail with reference to the accompanying drawings and embodiments. The following embodiments are merely intended to illustrate the present disclosure, but are not intended to limit the scope of the present disclosure.

Embodiment 1

Figures 1A, 1B:
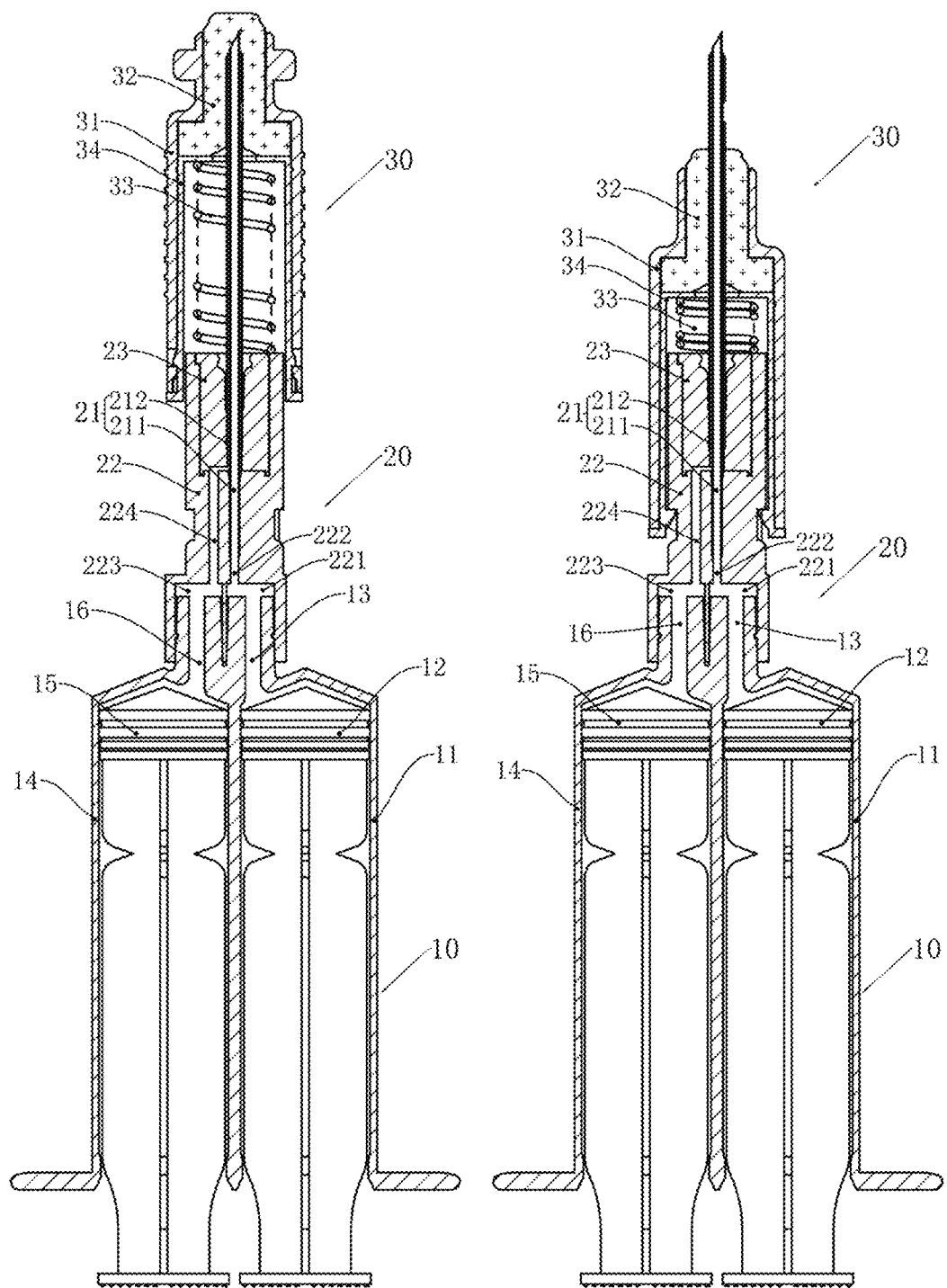
FIGS. 1A and 1B are a schematic sectional view of a medicine liquid transfer device in embodiment 1, where

As shown in FIGS. 1A and 1B, a closed type medicine liquid transfer device with double-chamber internal circulation includes a double-chamber syringe 10, a dispensing needle assembly 20, and a syringe needle sealing assembly 30.

The double-chamber syringe 10 consists of a first syringe barrel 11, a first piston rod 12 slidable back and forth along an inner cavity in the first syringe barrel 11, a second syringe barrel 14, and a second piston rod 15 slidable back and forth along the inner cavity in the second syringe barrel 14. The first syringe barrel 11 and the second syringe barrel 14 are each made of a transparent material, have the same dimensions, and are fixedly arranged in parallel, in the same direction and with flush front ends. Scales (not shown) are provided on a barrel surface of each syringe barrel to show the volume. On front end faces of the first syringe barrel 11 and the second syringe barrel 14, a first joint 13 and a second joint 16 are respectively provided adjacent to each other, where the two joints have the same structure, and each have an outer sidewall being a conical surface on which an annular boss (not shown) is provided.

The dispensing needle assembly 20 includes a dispensing needle 21 and a needle seat 22.

The dispensing needle 21 is a double-layer columnar structure consisting of an inner needle tube and an outer needle tube fixed to each other. The inner needle tube is longer than the outer needle tube, with both ends extending out of the outer needle tube, and a front end of the outer needle tube is fixedly connected to a front sidewall of the inner needle tube in a closed manner. A front end opening of the inner needle tube is an inclined opening, and a side opening is provided on a front end of the outer needle tube. In this manner, an inner cavity of the inner needle tube forms the inner columnar channel 211, and the side annular channel 212 is formed by a cavity between the outer needle tube and the inner needle tube.

A rear end of the needle seat 22 is provided with a first connection hole 221 matched in position and shape with the first joint 13, and a second connection hole 223 matched in position and shape with the second joint 16, and the needle seat 22 is internally provided with a first channel 222 and a second channel 224 in communication with the first connection hole 221 and the second connection hole 223 respectively and independent of each other. The first channel 222 is disposed coaxially with the dispensing needle 21, and the second channel 224 is disposed on one side of the first channel 222 in parallel.

The front end part of the needle seat 22 is provided with a mounting slot with an oval cross section, and the front end openings of the first channel 222 and the second channel 224 are both located at a bottom of the mounting slot. A needle penetrating table 23 with a configuration matched with the mounting slot is disposed in the mounting slot. A through pore channel is provided in the needle penetrating table 23 at a position corresponding to an axis of the dispensing needle 21, and consists of a front needle penetrating hole and a rear fixing hole. The needle penetrating hole is flared (for easy installation of the dispensing needle 21), with an inner diameter gradually reduced from front to back to the fixing hole, and an inner diameter of the fixing hole is matched with an outer diameter of the outer needle tube. The needle penetrating table 23 has a rear end face further provided with a communication slot having two ends in communication with the second channel 224 and the fixing hole, respectively.

The dispensing needle 21 is fixedly connected to the needle seat 22 with a rear end of the dispensing needle 21 embedded into the needle seat 22. In this case, the rear end of the inner needle tube penetrates through the pore channel in the needle penetrating table 23 to be fixed in the first channel 222 in an embedding manner; and a rear end of the outer needle tube penetrates the needle penetrating hole to be fixed in the fixing hole of the needle penetrating table 23 in an embedding manner.

By embedding the first joint 13 and the second joint 16 into the first connection hole 221 and the second connection hole 223, respectively, the dispensing needle assembly 20 is fixed and closely connected to the double-chamber syringe 10.

The syringe needle sealing assembly 30 includes a sheath 31, a closing member 32, an elastic member 33 and an inner sleeve 34 coaxially arranged.

A front end part of the sheath 31 has a smaller radial dimension to form a composite cylindrical structure consisting of a first cylindrical section with a smaller inner diameter and a second cylindrical section with a larger inner diameter. Two snap tables protruding radially outward are disposed symmetrically on an outer wall of the first cylindrical section, to enable fixed connection to the liquid transfer connector. Two snap holes are disposed symmetrically on a cylinder wall of the second cylindrical section close to the rear end opening.

The closing member 32 is made of silicone and has an inverted T-shaped cross section, a front diameter of the closing member 32 is equal to an inner diameter of the first cylindrical section of the sheath 31, a length of the closing member 32 is slightly larger than an axial length of the first cylindrical section, and a rear diameter is equal to an inner diameter of the second cylindrical section. While completely filling an inner cavity of the first cylindrical section and a front inner cavity of the second cylindrical section, the closing member 32 has a front end face protruding out of a front end face of the sheath 31. A pore channel for passage of the dispensing needle 21 is provided at a central axis of the closing member 32, and has an inner diameter smaller than an outer diameter of the dispensing needle 21.

An inner diameter and an outer diameter of inner sleeve 34 correspond to the outer diameter of the needle seat 22 and the inner diameter of the second cylindrical section of the sheath 31, respectively. A front end face of the inner sleeve is closed and has a through hole for passage of the dispensing needle 21 in a center of the end face. An annular boss is provided at a rear end opening in a radially outward mode, and two snaps matched with the snap holes are disposed symmetrically on an outer wall of the rear end opening.

The inner sleeve 34 is inserted into the second cylindrical section of the sheath 31, and the two are fixedly connected by the snaps matched with the snap holes. Meanwhile, the front end face of the inner sleeve 34 abuts against the rear end face of the closing member 32, so that the annular boss at the rear end is exposed to the sheath 31 and abuts against a rear end of the sheath 31.

The elastic member 33 is a spring in the inner sleeve 34, with two ends abutting against a front end inner surface of the inner sleeve 34 and a front end face of the needle seat 22.

Two L-shaped slots each consisting of an axial slot and a lateral slot are also formed symmetrically on a side face of the needle seat 22, and correspondingly, two sliding tables are symmetrically provided at the rear end of the inner sleeve 34 in a radially inward direction and embedded into and slidable along the respective L-shaped slots.

As shown in FIG. 1A, when the closed type medicine liquid transfer device is in a non-pressed state, the elastic member extends axially so that the sliding tables of the inner sleeve 34 are located on front ends of the axial slots on the side surface of the needle seat 22, the sheath 31 shields the dispensing needle 21 inside, and under an elastic force of silicone, the closing member 32 tightly wraps a front end part of the dispensing needle 21 and seals front channel openings of the inner columnar channel 211 and the side annular channel 212 inside.

In the closed type medicine liquid transfer device of FIG. 1A, the dispensing needle assembly 20 is fixed and closely connected to the double-chamber syringe 10, where the inner columnar channel 211, the first channel 222, the first connection hole 221 and the first syringe barrel 11 are sequentially communicated from front to back to form a closed passage I; and the side annular channel 212, the second channel 224, the second connection hole 223 and the second syringe barrel 14 are sequentially communicated from front to back to form a closed passage II. The closed passages I and II are independent of each other.

FIG. 1B is a schematic sectional view of the medicine liquid transfer device in an axially pressed state. In the pressed state, the spring is axially compressed, and the front end part of the dispensing needle 21, including the front channel openings of the inner columnar channel 211 and the side annular channel 212, penetrates out of the sheath 31 through the pore channel in the closing member 32. The sliding tables in the inner sleeve 34 slide backward synchronously along the axial slots, and moves into the lateral slots by rotating the double-chamber syringe 10 or the sheath 31, thereby limiting axial movement of the syringe needle sealing assembly 30 and achieving the effect of limiting and fixing.

FIGS. 2A and 2B are partial perspective sectional views of the medicine liquid transfer device in the non-pressed state and the pressed state.

Figure 3A:
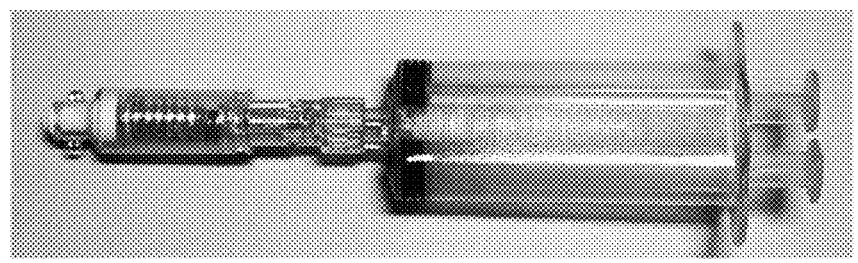
FIGS. 3A to 3C show a representative actual medicine liquid transfer device.
Figure 3B:
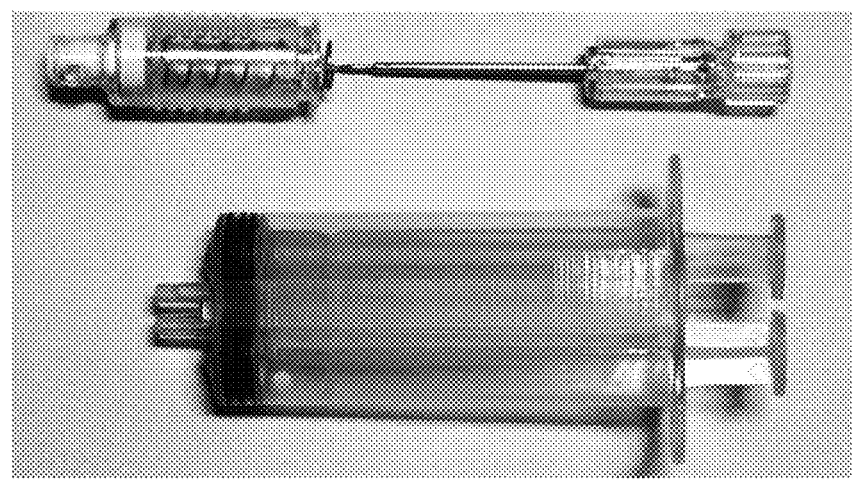
Figure 3C:
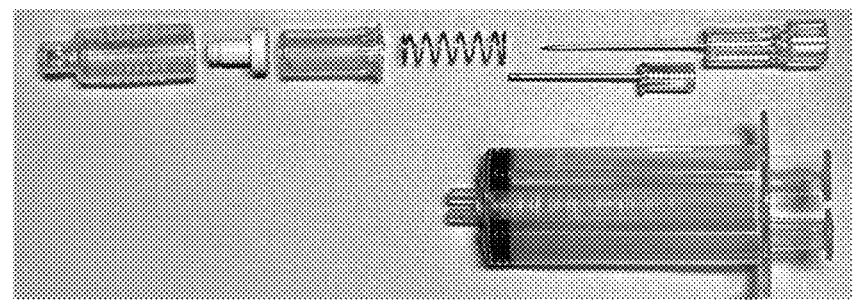

FIGS. 3A to 3C show a representative actual medicine liquid transfer device of the present disclosure. In the figures, FIG. 3A shows an actual sample in a standby state; FIG. 3B shows an actual sample in which the double-chamber syringe, the dispensing needle assembly and the syringe needle sealing assembly are disassembled from each other; and FIG. 3C shows an actual sample with disassembled components (where the inner and outer needle tubes of the dispensing needle are shown separated here for a more complete and clear illustration of the internal structure).

Embodiment 2

Figure 4A:
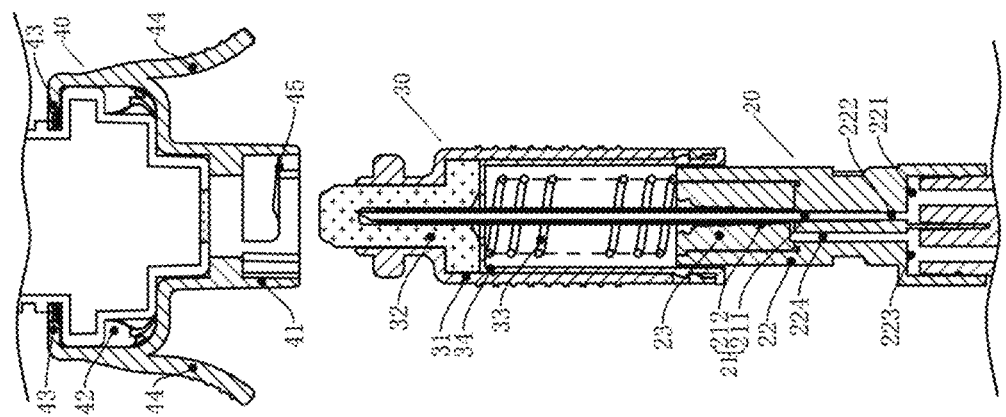
FIGS. 4A to 4C are a schematic sectional view of a medicine liquid transfer system in embodiment 2 with a medicine liquid transfer device and a liquid transfer connector, where
Figure 4B:
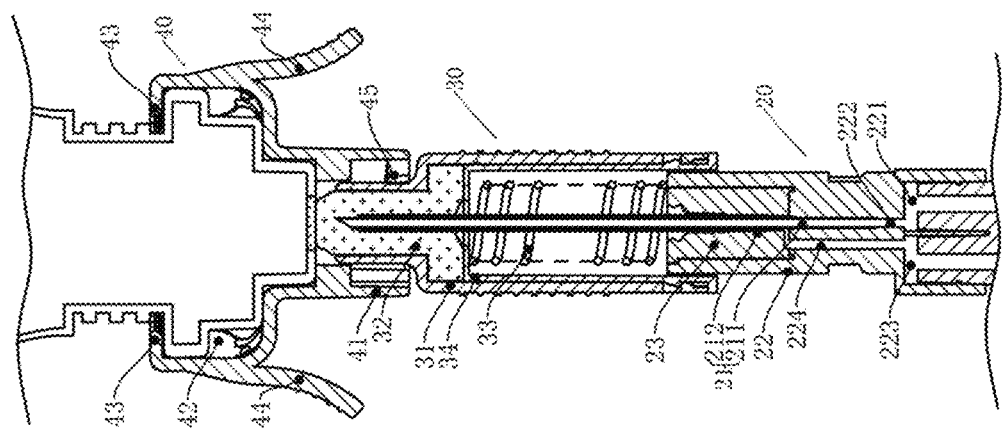
Figure 4C:
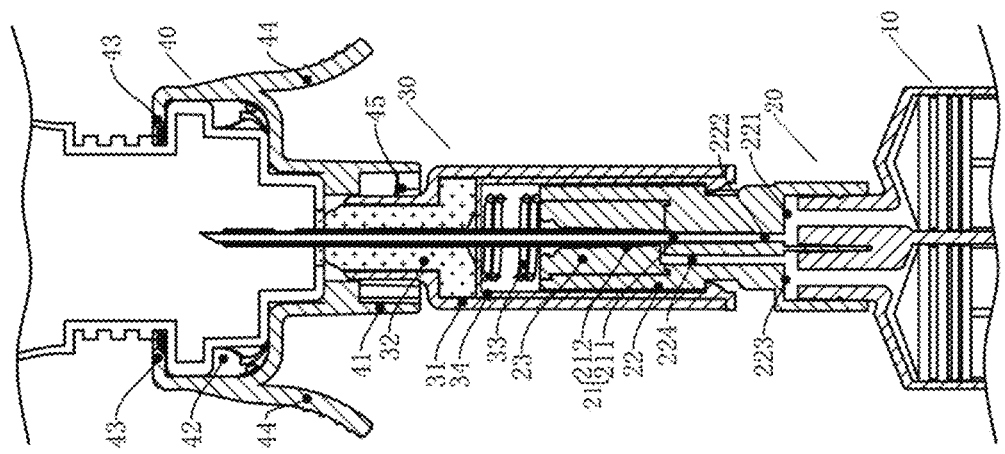

FIGS. 4A to 4C show a closed type medicine liquid transfer system, including a closed type medicine liquid transfer device with double-chamber internal circulation (as shown in FIGS. 1A to 3C: not fully shown in FIGS. 4A to 4C), and a liquid transfer connector 40 configured to fixedly connecting the medicine liquid transfer device to a medicine container.

The liquid transfer connector 40 includes a first sleeve 41 and a second sleeve 42 coaxially arranged and connected with each other.

The first sleeve 41 is configured to be detachably sleeved onto a front end of a sheath 31 of the medicine liquid transfer device. Corresponding to the snap tables on the front end outer wall of the sheath 31, two snap slots 45, each having an L-shaped structure consisting of an axial slot and a lateral slot, are disposed symmetrically on an inner wall of the first sleeve 41. When the sheath 31 is inserted into the first sleeve 41, the snap tables enters the axial slots of the snap slots synchronously, and when the sheath reaches a preset position, the medicine liquid transfer device is rotated to enable the snap tables to rotate into the lateral slots, so that the medicine liquid transfer device is fixed to the liquid transfer connector.

The second sleeve 42 is configured to be detachably sleeved onto the container opening of the medicine container. Snap claws 43 extending forward axially are disposed symmetrically on outer edges of the second sleeve 42, release arms 44 extending backward are provided on rear ends of the respective snap claws 43, and the second sleeve 42 is fixed to the container opening by the snap claws 43 and removable from the container opening by the release arms 44.

When the medicine liquid transfer device is fixedly connected to the medicine container by the liquid transfer connector 40, the front end face of the closing member 32 and the container opening of the medicine container are stably abutted in the sleeves.

In the medicine liquid transfer system shown in FIG. 4A, the medicine liquid transfer device and the liquid transfer connector are not connected. FIG. 4B is a schematic sectional view of the medicine liquid transfer system in a state where the medicine liquid transfer device and the liquid transfer connector are connected. FIG. 4C is a schematic sectional view of the medicine liquid transfer system in an operating state.

Figure 5C:
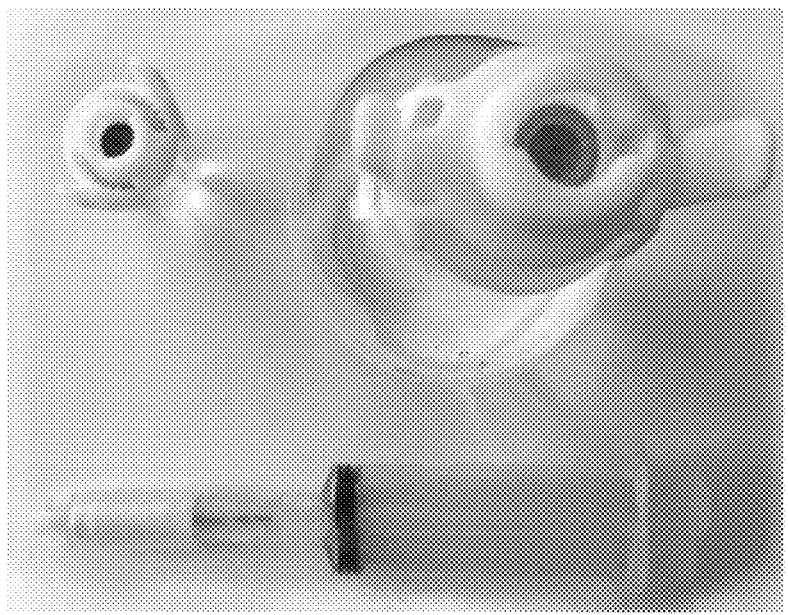
FIGS. 5A to 5C show a representative actual medicine liquid transfer system.
Figure 5B:
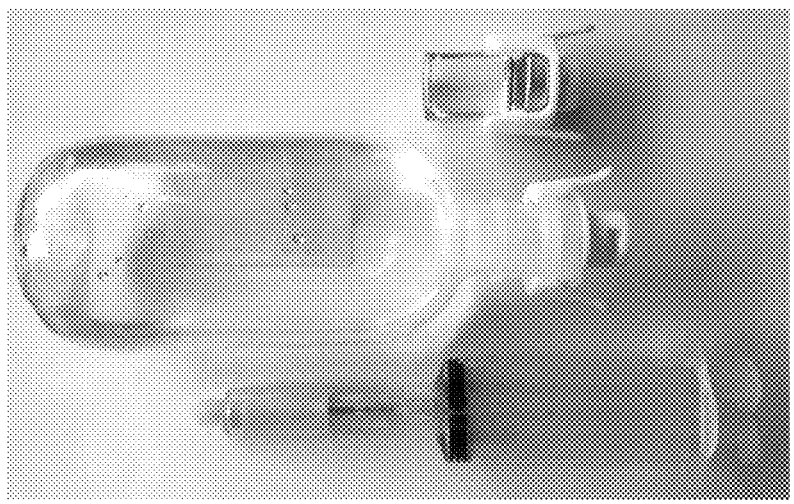
Figure 5A:
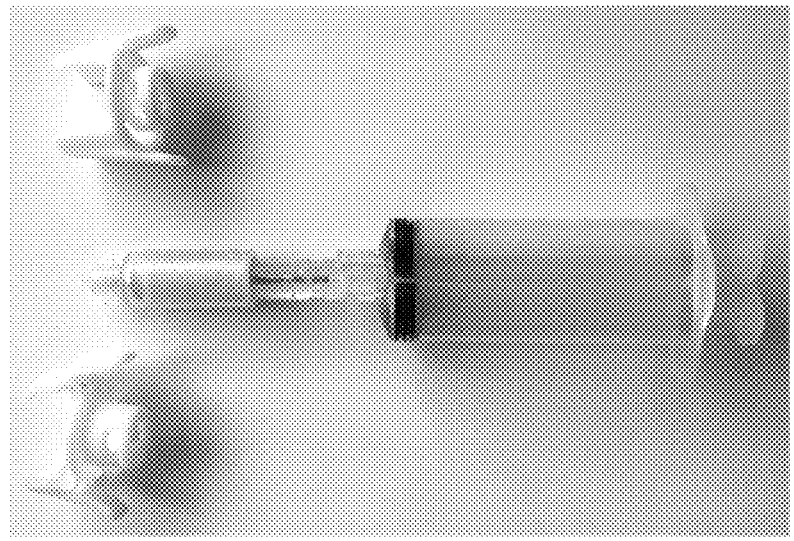

FIGS. 5A to 5C show a representative actual medicine liquid transfer system of the present disclosure. In the figures, FIG. 5A shows an actual sample in a standby state; and FIGS. 5B and 5C show an actual sample from different angles when the liquid transfer connector is fixedly connected to an infusion bottle and a penicillin bottle.

Application Embodiment 1

The performance advantages of the medicine liquid transfer device and medicine liquid transfer system of the present disclosure over the existing art have been described in detail above. To further verify the technical effects, application experiments are performed on actual products.

1. Experimental Location

Product Development Laboratory of Zhanjiang Jianliyuan Medical Supplies Co., LTD.

2. Experimental Subject

The medicine liquid transfer system shown in FIGS. 5A to 5C is taken as an experimental sample, in which the medicine liquid transfer device is as shown in FIGS. 3A to 3C, and the first and second syringe barrels each have a size of 20 mL.

A penicillin bottle is filled with 10 mL of a fluorescein sodium aqueous solution at a concentration of 10 g/L, sealed with an aluminum cap chlorinated butyl rubber plug, and marked as penicillin bottle A. Another empty penicillin bottle is taken and also sealed with an aluminum cap chlorinated butyl rubber plug, and marked as penicillin bottle B. The two bottles are reserved for later use.

3. Experimental Method

The method includes: 1) pulling a first piston rod of the double-chamber syringe backward, until a volume of a front cavity of the first syringe barrel is larger than 10 mL, where to complete this operation of storing air, the double-chamber syringe may be separated from the dispensing needle assembly, and then fixedly connected to the dispensing needle assembly again after the air storage;

2) sleeving a second sleeve of a liquid transfer connector A on a mouth of a penicillin bottle A and fixing the two with snap claws, and then holding the sheath of the medicine liquid transfer device to align the sheath with a first sleeve inserted into the liquid transfer connector A, and rotating the sheath to fix, in which case a front end face of the closing member abuts against a rubber opening of the penicillin bottle A in the sleeves;

3) holding and pushing forward a syringe barrel of the medicine liquid transfer device, so that the dispensing needle penetrates through the closing member into the penicillin bottle A with compression of the spring, and rotating the syringe barrel when the dispensing needle is completely penetrated in, so that the syringe needle sealing assembly is limited and fixed to the needle seat;

4) pulling a second piston rod of the double-chamber syringe to extract the solution from the penicillin bottle A to the second syringe barrel through the closed passage II, in which case a negative pressure is generated in the penicillin bottle A, and so that the first piston rod is moved forward under an action of an internal and external pressure difference, and the air reserved in the first syringe barrel is supplemented into the penicillin bottle A until the internal and external air pressures are balanced;

5) rotating the syringe barrel reversely when the solution is extracted, to release the limiting and fixing of the syringe needle sealing assembly and the needle seat, and moving the double-chamber syringe and the dispensing needle assembly backward under an elastic potential energy of the spring until the dispensing needle is reset, that is, until the dispensing needle is withdrawn from the penicillin bottle A and sealed by the closing member again;

6) screwing a sheath of the medicine liquid transfer device to release the fixed connection between the medicine liquid transfer device and the liquid transfer connector A, and pulling the medicine liquid transfer device from the liquid transfer connector A;

7) sleeving a second sleeve of a liquid transfer connector B on a mouth of a penicillin bottle B and fixing the two with snap claws, and then holding the sheath of the medicine liquid transfer device to align the sheath with a first sleeve inserted into the liquid transfer connector B, and rotating the sheath to fix, in which case a front end face of the closing member abuts against a rubber opening of the penicillin bottle B in the sleeves;

8) holding and pushing forward a syringe barrel of the medicine liquid transfer device, so that the dispensing needle penetrates through the closing member into the penicillin bottle B with compression of the spring, and rotating the syringe barrel when the dispensing needle is completely penetrated in, so that the syringe needle sealing assembly is limited and fixed to the needle seat;

9) pushing a second piston rod of the double-chamber syringe so that the solution is injected into the penicillin bottle B from the second syringe barrel through a closed passage II, in which case a positive pressure is generated in the penicillin bottle B, and air in the penicillin bottle automatically enters the first syringe barrel through the closed passage I to push the first piston rod to move backward;

10) when the solution is completely injected into the penicillin bottle B, referring to steps (5) and (6), resetting the dispensing needle and pulling the medicine liquid transfer device out of the liquid transfer connector B, and using a three-purpose UV analyzer (ZF-1) to test the medicine liquid transfer system at different links of the process. The specific method includes: placing the medicine liquid transfer system on an operation desk of the three-purpose UV analyzer, and starting the device to irradiate the medicine liquid transfer system with UV light, and observing whether fluorescent spots appear in a specific region.

4. Experimental Result

Figure 6A:
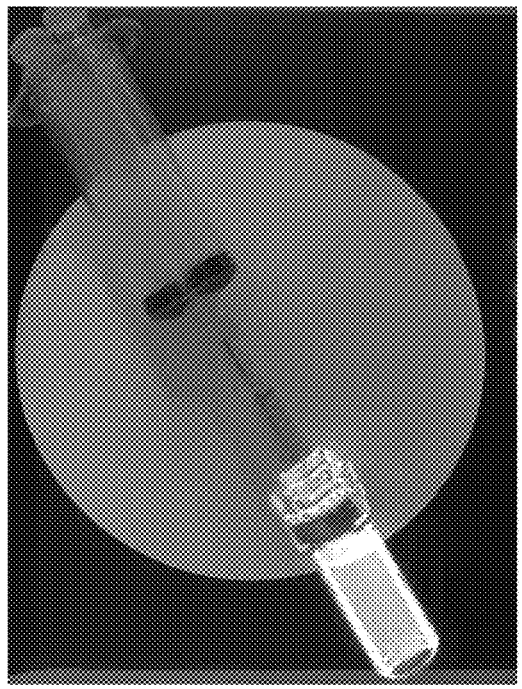
FIGS. 6A to 6C show actual test results obtained by a three-purpose UV analyzer in application embodiment 1.
Figure 6B:
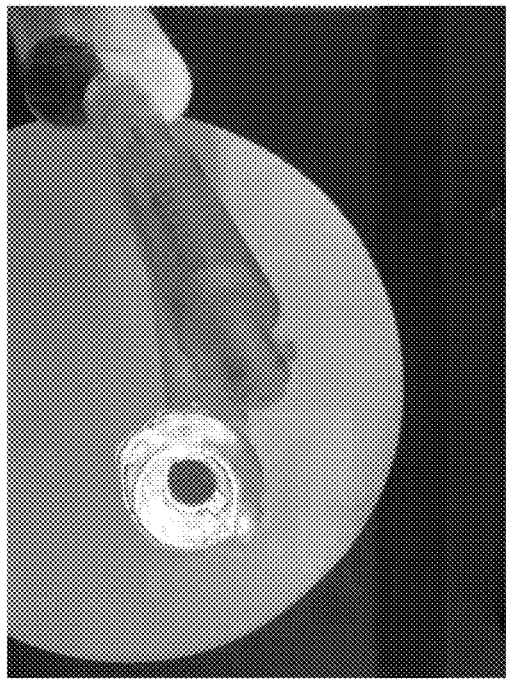
Figure 6C:
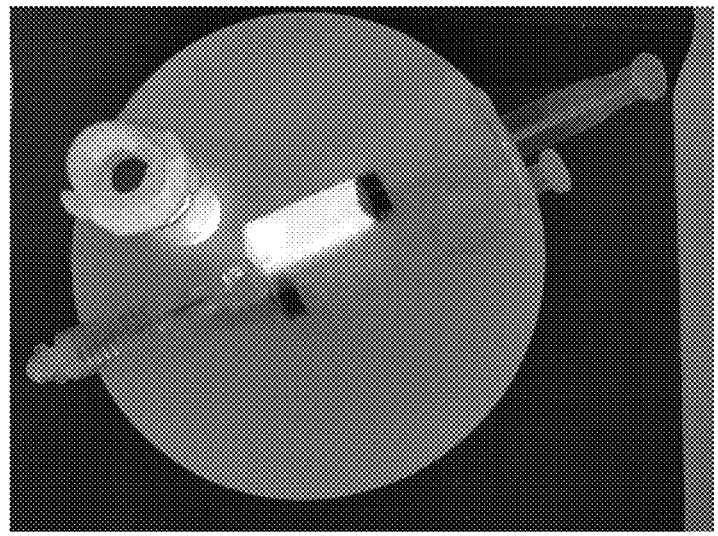

Test results obtained by the three-purpose UV analyzer are shown in FIGS. 6A to 6C.

FIG. 6A is a fluorescent display diagram of the medicine liquid transfer device after the liquid transfer connector A is fixedly connected to the penicillin bottle A, which shows an initial fluorescent state upon connection. Note: the first syringe barrel is not pre-stored with air since the only purpose is to show the initial fluorescent state.

FIG. 6B is a fluorescent display diagram of the medicine liquid transfer system after steps 1) to 6) are completed. It can be seen that: there is no fluorescence at a contact part of the penicillin bottle A and the medicine liquid transfer device. This shows that the extraction of the fluorescein sodium aqueous solution is completed under the condition of complete sealing, the medicine liquid transfer system has excellent leak-proofness, and no leakage happens at the contact part of the penicillin bottle A and the medicine liquid transfer device.

FIG. 6C is a fluorescent display diagram of the system in the process of step 9), where after part of the fluorescein sodium aqueous solution is injected into the penicillin bottle B, the operation is suspended and the medicine liquid transfer device is separated from the liquid transfer connector B. As can be seen, there is no fluorescence at a contact part of the penicillin bottle B and the medicine liquid transfer device. In the medicine liquid transfer device, no fluorescence appears on the appearance of the sample except scarce transmissive fluorescence caused by the second syringe barrel filled with the fluorescein sodium aqueous solution and the residual solution inside the liquid channel. These indicate that the medicine liquid transfer system of the present disclosure has excellent leak-proofness, and the closed passages I and II each perform their own functions without interfering with each other.

In addition, when the medicine liquid transfer system of the present disclosure is used, the pressure inside and outside the penicillin bottle can be ensured to be constantly equal, so that the solution extraction and injection art very smooth, and the problem of difficult operation caused by the requirement of overcoming an internal and external pressure difference of the penicillin bottle does not exist.

Application Embodiment 2

To further verify the leak-proofness of the medicine liquid transfer device and the medicine liquid transfer system of the present disclosure in the medicine liquid preparation and transfer process, an application experiment is performed with an odorous solution.

1. Experimental Location

Product Development Laboratory of Zhanjiang Jianliyuan Medical Supplies Co., LTD.

2. Experimental Subject

The medicine liquid transfer system shown in FIGS. 5A to 5C is taken as an experimental sample, in which the medicine liquid transfer device is as shown in FIGS. 3A to 3C, and the first and second syringe barrels each have a size of 20 mL.

In a fume hood in the laboratory, A penicillin bottle is filled with 10 mL of a garlic odorant solution at a concentration of 0.1 g/L, sealed with an aluminum cap chlorinated butyl rubber plug, and fully cleaned at an outer surface and dried to remove other odors, and marked as penicillin bottle A. Another empty penicillin bottle is taken and also sealed with an aluminum cap chlorinated butyl rubber plug, and marked as penicillin bottle B. The two bottles are reserved for later use.

3. Experimental Method

In a separate and closed laboratory with an area of about 12 square meters and referring to the steps in application embodiment 1, the garlic odorant solution in the penicillin bottle A are completely transferred to the penicillin bottle B.

Then, three men and three women aged 26 to 43 with good health and normal smell are selected and enter the laboratory for 30 seconds, and then give feedback about the corresponding odor and a degree thereof.

4. Experimental Result

The feedback results show that: among the 6 persons in test, 3 men and 2 women declared that they did not smell any odor; while I woman declared that there appeared to be a very slight odor in the air, but she could not determine what odor it was. This result further proves the fully-closed effect of the medicine liquid transfer system of the present disclosure in the medicine liquid preparation and transfer process, which can minimize the risk of medicine leakage and provide an excellent leakproof effect.

The foregoing embodiments have been primarily described in terms of the basic principles, features and advantages of the present disclosure. It will be understood by those skilled in the art that the present disclosure is not limited to the embodiments described above, and the above embodiments and description are described only for the purpose of illustrating the present disclosure. Various changes and modifications may be made without departing from the spirit and scope of the present disclosure, and such changes and modifications all fall within the scope of the present disclosure as claimed.

What is claimed is:

1. A closed type medicine liquid transfer device with double-chamber internal circulation, comprising:
   a double-chamber syringe;
   a dispensing needle assembly; and
   a syringe needle sealing assembly,
   wherein the double-chamber syringe consists of:
      a first syringe barrel;
      a first piston rod slidable back and forth along an inner cavity in the first syringe barrel;
      a second syringe barrel; and
      a second piston rod slidable back and forth along the inner cavity in the second syringe barrel,
      wherein the first syringe barrel and the second syringe barrel are fixedly arranged in parallel, in the same direction and with flush front ends,
      a first joint is provided on a front end face of the first syringe barrel, and
      a second joint is provided on a front end face of the second syringe barrel,
   wherein the dispensing needle assembly comprises:
      a dispensing needle; and
      a needle seat,
      wherein the dispensing needle is fixedly connected to the needle seat with a rear end of the dispensing needle embedded into a front end of the needle seat,
      a rear end of the needle seat is provided with a first connection hole matched with the first joint and a second connection hole matched with the second joint, and
      the needle seat is internally provided with a first channel and a second channel in communication with the first connection hole and the second connection hole, respectively and independent of each other;
      the dispensing needle is a double-layer columnar structure including an inner columnar channel and a side annular channel,
      wherein the inner columnar channel is in communication with the first channel, and the side annular channel is in communication with the second channel,
      the dispensing needle consists of an inner needle tube and an outer needle tube, the inner needle tube is inserted in the outer needle tube, with both ends extending out of the outer needle tube, so that the inner columnar channel is formed by an inner cavity of the inner needle tube, and the side annular channel is formed by a cavity between the outer needle tube and the inner needle tube, and
      the dispensing needle assembly is fixed and closely connected to the double-chamber syringe by embedding the first joint and the second joint into the first connection hole and the second connection hole, respectively;
   wherein the syringe needle sealing assembly includes:
      a sheath, a closing member and an elastic member arranged coaxially with the dispensing needle,
      the sheath is a hollow cylindrical structure with front and back openings, and is movable axially and sleeved onto the front end of the needle seat,
      the closing member is made of an elastic material, and fixedly disposed inside a front barrel of the sheath; a pore channel for passage of the dispensing needle is provided at a central axis of the closing member, and has an inner diameter smaller than an outer diameter of the dispensing needle,
      the elastic member is provided between the closing member and the needle seat, and provides axial elastic support for the closing member at the front end against the needle seat,
      in a non-pressed state, the elastic member extends axially so that the sheath shields the dispensing needle inside, and under an elastic force of the elastic material, the closing member tightly wraps a front end part of the dispensing needle and seals front channel openings of the inner columnar channel and the side annular channel inside; and
      in a pressed state, the elastic member is axially compressed, and the front end part of the dispensing needle, including the front channel openings of the inner columnar channel and the side annular channel, penetrates out of the sheath through the pore channel in the closing member.

2. The closed type medicine liquid transfer device of claim 1, characterized in that:
the first joint and the second joint each have an outer sidewall being a conical surface on which at least one annular boss is provided; and
accordingly, the first connection hole and the second connection hole at the rear end of the needle seat each have a shape matched with the conical surface of the corresponding joint, and have a wall provided with an annular slot corresponding to the annular boss.

3. The closed type medicine liquid transfer device of claim 1, characterized in that: the inner needle tube and the outer needle tube are independent of each other, or integrally formed and fixedly connected with each other.

4. The closed type medicine liquid transfer device of claim 3, characterized in that: the front end of the inner needle tube is provided as an inclined opening, or the front end of the inner needle tube is a pointed end provided with a side opening; and the front sidewall of the outer needle tube is provided with a side opening.

5. The closed type medicine liquid transfer device of claim 1, characterized in that:
a front end part of the needle seat is provided with a mounting slot, in which a needle penetrating table with a configuration matched with the mounting slot is disposed;
the front end openings of the first channel and the second channel are both located at a bottom of the mounting slot, and the front end opening of the first channel is coaxial with the dispensing needle;
a through pore channel in a front-rear direction is provided in the needle penetrating table at a position corresponding to an axis of the dispensing needle, and consists of a front needle penetrating hole and a rear fixing hole, wherein the needle penetrating hole is flared, with an inner diameter gradually reduced from front to back to the fixing hole, and an inner diameter of the fixing hole is matched with an outer diameter of the outer needle tube;
the needle penetrating table has a rear end face provided with a communication slot having two ends in communication with the second channel and the fixing hole, respectively;
a rear end of the inner needle tube of the dispensing needle penetrates through the needle penetrating table to be fixed in the first channel in an embedding manner; and a rear end of the outer needle tube is fixed in the fixing hole of the needle penetrating table in an embedding manner.

6. The closed type medicine liquid transfer device of claim 5, characterized in that: the first channel in the needle seat is disposed coaxially with the dispensing needle, and the second channel is disposed on one side of the first channel in parallel.

7. The closed type medicine liquid transfer device of claim 5, characterized in that: the needle penetrating table has a non-circular cross section that remains unchanged in an axial direction.

8. The closed type medicine liquid transfer device of claim 1, characterized in that: when the dispensing needle assembly is fixed and closely connected to the double-chamber syringe, the inner columnar channel, the first channel, the first connection hole and the first syringe barrel are sequentially communicated from front to back to form a closed passage I; the side annular channel, the second channel, the second connection hole and the second syringe barrel are sequentially communicated from front to back to form a closed passage II; and the closed passages I and II are independent of each other.

9. The closed type medicine liquid transfer device of claim 1, characterized in that, the syringe needle sealing assembly includes a sheath, a closing member, an elastic member and an inner sleeve coaxially arranged, wherein:
a front end part of the sheath has a smaller radial dimension to form a composite cylindrical structure consisting of a first cylindrical section with a smaller inner diameter and a second cylindrical section with a larger inner diameter;
the closing member is designed as a structure having an inverted T-shaped cross section with a front diameter corresponding to the inner diameter of the first cylindrical section and a rear diameter corresponding to the inner diameter of the second cylindrical section, so that the closing member is capable of at least partially filling an inner cavity of the second cylindrical section while completely filling an inner cavity of the first cylindrical section;
an inner diameter of the inner sleeve corresponds to the outer diameter of the needle seat, an outer diameter of the inner sleeve corresponds to the inner diameter of the second cylindrical section of the sheath, and a front end face of the inner sleeve is closed and has a through hole for passage of the dispensing needle in a center of the end face; the inner sleeve is fixedly connected in the second cylindrical section of the sheath, with the front end face abutting against a rear end face of the closing member; and
the elastic member is provided in the inner sleeve, with two ends abutting against a front end inner surface of the inner sleeve and a front end face of the needle seat.

10. The closed type medicine liquid transfer device of claim 9, characterized in that: a snap is provided on an outer wall of the inner sleeve and a corresponding snap hole is provided in the second cylindrical section of the sheath, so that when the inner sleeve is inserted into the sheath, the sheath is fixedly connected to the inner sleeve by the snap matched with the snap hole.

11. The closed type medicine liquid transfer device of claim 9, characterized in that: an annular boss is provided at a rear end opening of the inner sleeve in a radially outward mode, and when the front end face of the inner sleeve abuts against the rear end face of the closing member, the annular boss at the rear end is exposed to the sheath and abuts against a rear end of the sheath.

12. The closed type medicine liquid transfer device of claim 9, characterized in that: snap structures are provided on both the front end inner surface of the inner sleeve and the front end face of the needle seat to enable fixed connection to the elastic member.

13. The closed type medicine liquid transfer device of claim 9, characterized in that: an L-shaped slot consisting of an axial slot and a lateral slot is formed on a side face of the needle seat, and a sliding table is provided at the rear end of the inner sleeve in a radially inward direction and embedded into and slidable along the L-shaped slot.

14. The closed type medicine liquid transfer device of claim 1, characterized in that: a front end face of the closing member protrudes out of a front end face of the sheath.

15. The closed type medicine liquid transfer device of claim 1, characterized in that: two snap tables protruding radially outward are disposed symmetrically on a front end outer wall of the sheath to enable fixed connection to a liquid transfer connector.

16. A closed type medicine liquid transfer system, comprising:
the closed type medicine liquid transfer device of claim 1, and a liquid transfer connector configured to fixedly connect the medicine liquid transfer device to a medicine container; wherein
one end of the liquid transfer connector is configured to fixedly connect the medicine container in a detachable manner, and the other end of the liquid transfer connector is configured to fixedly connect the medicine liquid transfer device in a detachable manner; and in fixed connection, a front end face of a closing member abuts against a container opening of the medicine container.

17. The closed type medicine liquid transfer system of claim 16, characterized in that: the liquid transfer connector includes a first sleeve and a second sleeve coaxially arranged and connected with each other, wherein the first sleeve is configured to be detachably sleeved onto a front end of a sheath of the medicine liquid transfer device, and the second sleeve is configured to be detachably sleeved onto the container opening of the medicine container, and in fixed connection, the front end face of the closing member and the container opening of the medicine container are stably abutted in the sleeves.

18. The closed type medicine liquid transfer system of claim 17, characterized in that: snap claws extending forward axially are disposed symmetrically on outer edges of the second sleeve, release arms extending backward are provided on rear ends of the respective snap claws, and the second sleeve is fixed to the container opening by the snap claws and removable from the container opening by the release arms.

19. The closed type medicine liquid transfer system of claim 17, characterized in that: two snap slots, each having an L-shaped structure consisting of an axial slot and a lateral slot, are disposed symmetrically on an inner wall of the first sleeve, and correspondingly, two snap tables protruding radially outward are disposed symmetrically on a front end outer wall of the sheath.

20. The closed type medicine liquid transfer device of claim 3, characterized in that: when the inner needle tube and the outer needle tube are integrally formed and fixedly connected with each other, a front end of the outer needle tube is fixedly connected to a front sidewall of the inner needle tube in a closed manner.

* * * * *